United States Patent
Kimura et al.

(10) Patent No.: US 6,469,165 B1
(45) Date of Patent: Oct. 22, 2002

(54) PROCESS FOR PREPARATION OF POLYAMINOTRIAZINES

(75) Inventors: Kenji Kimura, Osaka (JP); Shinya Tanaka, Osaka (JP); Manji Sasaki, Hyogo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 08/363,780

(22) Filed: Dec. 27, 1994

(30) Foreign Application Priority Data

| Dec. 24, 1993 | (JP) | 5-329084 |
| Jul. 1, 1994 | (JP) | 6-151220 |
| Jul. 1, 1994 | (JP) | 6-151221 |

(51) Int. Cl.⁷ .................................... C07D 251/70
(52) U.S. Cl. ..................... 544/198; 544/209
(58) Field of Search ................... 544/198, 209

(56) References Cited

U.S. PATENT DOCUMENTS

| 4,086,204 A | | 4/1978 | Cassandrini et al. | 544/198 |
| 4,104,248 A | | 8/1978 | Cantatore | 546/184 |
| 4,315,859 A | * | 2/1982 | Nikles | 544/209 |
| 4,331,586 A | | 5/1982 | Hardy | 544/113 |
| 4,335,242 A | | 6/1982 | Wiezer et al. | 544/209 |
| 4,409,348 A | | 10/1983 | Wiezer et al. | 524/100 |
| 4,492,791 A | | 1/1985 | Orban et al. | 544/198 |
| 4,528,374 A | * | 7/1985 | Nikles | 546/186 |
| 4,547,538 A | | 10/1985 | Lai et al. | 524/100 |
| 4,605,743 A | | 8/1986 | Malz, Jr. et al. | 546/186 |
| 4,607,104 A | | 8/1986 | Malz, Jr. et al. | 546/186 |
| 4,639,479 A | | 1/1987 | Lai et al. | 524/100 |
| 4,722,806 A | | 2/1988 | Lai et al. | 252/403 |
| 5,189,173 A | | 2/1993 | Lai et al. | 546/244 |
| 5,270,471 A | | 12/1993 | Lai et al. | 546/244 |
| 5,322,947 A | | 6/1994 | Tanaka et al. | 546/186 |

FOREIGN PATENT DOCUMENTS

| EP | A1-065169 | | 11/1982 |
| EP | 0177229 | * | 8/1984 |
| EP | A2-302020 | | 2/1989 |
| EP | A3-357223 | | 3/1990 |
| EP | A3-377324 | | 7/1990 |
| EP | A1-508940 | | 10/1992 |
| EP | A3-093693 | | 11/1993 |
| FR | 2333821 | | 7/1977 |
| WO | 8302943 | | 9/1983 |

* cited by examiner

*Primary Examiner*—John M. Ford
*Assistant Examiner*—Venkataraman Balasubramanian
(74) *Attorney, Agent, or Firm*—Fitch, Even, Tabin & Flannery

(57) ABSTRACT

Polyaminotriazines represented by formula (I) can be prepared by conducting a reduction alkylamination of a tetramethylpiperidone with a diamine represented by formula (IIb), $NH_2$—R—$NH_2$, in the presence of a hydrogenating catalyst, removing the catalyst upon completion of the reaction to obtain an unrefined crude product (A); and, conducting a polycondensation reaction of the unrefined crude product (A) and a dichlorotriazine in an aromatic solvent and in the presence of an inorganic base.

17 Claims, No Drawings

PROCESS FOR PREPARATION OF POLYAMINOTRIAZINES

FIELD OF THE INVENTION

The present invention relates to an improved process for preparing linear polyaminotriazines. More particularly, polyaminotriazines represented by the formula (I):

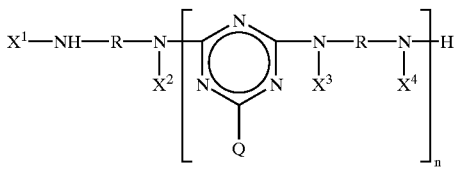

wherein n is a number from 2 up to 20; $X^1$, $X^2$, $X^3$ and $X^4$, which are same or different, are each hydrogen or a piperidyl represented by formula (Ia):

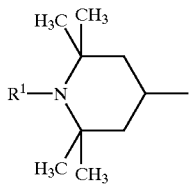

wherein $R^1$ is a hydrogen atom, $C_1$ to $C_{12}$ alkyl, $C_1$ to $C_{18}$ alkoxy, $C_3$ to $C_8$ alkenyl, $C_7$ to $C_{11}$ arylalkyl or $C_3$ to $C_5$ alkenyloxy, provided that 75 mole % or more of $X^1$, $X^2$, $X^3$ and $X^4$ is piperidyl represented by formula (Ia); R is $C_2$ to $C_{12}$ alkylene which can be interrupted by —O— or —$NR^2$—, wherein $R^2$ is hydrogen, $C_1$ to $C_{12}$ alkyl, $C_3$ to $C_{12}$ cycloalkyl or a piperidyl represented by formula (Ia), or R is a divalent $C_6$ to $C_{15}$ cycloaliphatic group; and Q is —$OR^3$, —$NHR^4$ or —$NR^4R^5$, wherein $R^3$ is $C_1$ to $C_{12}$ alkyl, $C_5$ to $C_{12}$ cycloalkyl, benzyl, phenyl, tolyl or piperidyl represented by formula (Ia), $R^4$ is $C_1$ to $C_{12}$ alkyl, $C_3$ to $C_{12}$ alkoxyalkyl, $C_4$ to $C_{12}$ N,N-dialkylaminoalkyl, $C_3$ to $C_5$ alkenyl, phenyl, benzyl, cyclohexyl, tolyl or piperidyl represented by formula (Ia), and $R^5$ is $C_1$ to $C_{12}$ alkyl or cycloalkyl, or $R^4$ and $R^5$ together form a tetra or pentamethylene group (e.g. together with the N atom to which they are bonded, $R^4$ and $R^5$ form a 5- or 6-membered heterocyclic ring) are prepared in accordance with the present invention.

These compounds are useful as light stabilizers for organic materials, and are particularly useful for stabilizing synthetic resins.

BACKGROUND OF THE INVENTION

It is known that organic materials, such as synthetic polymers, i.e., polyethylene, polypropylene or the like, are liable to undergo a deterioration of their properties, such as softening, embrittlement and discoloration, when they are exposed to light. In order to prevent such deterioration, various stabilizers, including polyaminotriazines, have been proposed.

Various methods for preparing polyaminotriazines are known to those skilled in the art.

According to JP-A-52-71486, polyaminotriazines are usually prepared by polycondensation of a monopiperidylamine or dipiperidylamine represented by the formula (II):

$$X—NH—R—NH—X^5 \quad (II)$$

wherein R can be as defined above, X can be piperidyl represented by formula (Ia) and $X^5$ can be hydrogen or piperidyl represented by formula (Ia), with a dichlorotriazine represented by formula (III):

wherein Q can be as defined above, in an inert solvent from −10° C. up to the solvent boiling temperature in the presence of an inorganic or organic base.

In more detail, this reaction is carried out mainly in toluene under refluxing conditions and in the presence of sodium hydroxide. Since the reaction mixture contains water generated from the reaction, the reflux is usually actually conducted at a temperature about 10° C. lower than the boiling point of toluene. The polyaminotriazines are obtained from the resultant reaction mixture by filtering off the by-products and sodium chloride, and by evaporating off the solvent.

The process of JP-A-52-71486, however, is disadvantageous in that the reaction hardly proceeds to completion, and that sparingly soluble by-products having a high melting point are formed. These by-products are sparingly soluble in the synthetic resins to be stabilized by the polyaminotriazines. These by-products can deteriorate the synthetic resins, and thus reduce the commercial value of the resin products. As a consequence, the conventionally produced polyaminotriazines containing the by-products are undesirable as stabilizers. Therefore, to obtain useful stabilizers, it has proven necessary to remove the by-product contaminants from the resulting reaction mixture, such as by filtration. However, the separation can drastically and adversely reduce the yield. For instance, the polyaminotriazine yield decreases to only about 70–75% after the by-products, at least some of which are fine powdery materials, have been separated off by filtration.

The process of JP-A-52-71486 has yet another disadvantage in that only polycondensates having relatively low polycondensation degree of less than 6 are reportedly obtained. These polyaminotriazines are not particularly desired for use as stabilizers. Polyaminotriazines having a polycondensation degree of 6 or more are preferred, and a polycondensation degree of 7 to 11 is even more preferred, when the compounds are used as a stabilizer for a synthetic resin exposed to the atmosphere (open air) or the like.

Another process for the preparation of polyaminotriazines is described in JP-A-58-210820. According to JP-A-58-201820, the polyaminotriazines represented by formula (I) are prepared by a polycondensation of a dichlorotriazine represented by formula (III), which is obtained by a substitution of a chlorine atom of cyanuric chloride with a radical such as amine, with a diamine represented by formula (II) in a water-immiscible inert solvent at a temperature of from 140° C. to 220° C. at an elevated pressure in the presence of an aqueous solution of an inorganic base.

In an example of the process of JP-A-58-210820, the polycondensation reaction is conducted in a two-phase system of xylene/water at an elevated pressure at a temperature of about 185° C. in the presence of a concentrated aqueous solution of sodium hydroxide. The resultant reaction mixture is subjected to phase-separation, washing and oil-water separation to obtain a xylene phase, which is, then, filtered to remove the by-products.

Polyaminotriazines are obtained from the resulting filtrate by evaporating off the solvent. According to this known process, the polyaminotriazine may be obtained at a theoretical yield of 93–96% based on the amount of the diamine of formula (II), but nonetheless there are several significant disadvantages.

One disadvantage is that a special and high-priced material which is alkaline- and heat-resistant must be used for the reaction vessel because the reaction is carried out at high temperature, under alkaline conditions, under high pressure, and in the presence of water. These conditions are so severe that even SUS 316L, which has been widely used for pressure reaction vessels, is eroded. Therefore, even SUS 316L cannot be used for the reaction vessel.

Another disadvantage is that polyaminotriazine products having a low polycondensation degree are liable to be obtained because the reaction components can come in contact with water. The chlorotriazine intermediate of this reaction is hydrolyzed at a high temperature of about 185° C. when it comes in contact with water. However, in this known process, the reaction is carried out in a two-phase system which includes water.

Hitherto, in addition to the already noted drawbacks, the preparation of the polyaminotriazines represented by formula (I) from the diamine represented by formula (II) and the dichlorotriazine represented by formula (III) has been carried out independently from the preparation of the diamine represented by formula (II). For instance, conventionally, the dipiperidylamine represented by formula (II) is prepared by a reaction between a tetramethylpiperidone represented by formula (IIa) and diamine represented by formula (IIb) has been isolated from the resulting reaction mixture before being used for the preparation of the polyaminotriazines represented by formula (I). More particularly, the diamine represented by formula (II) has been prepared by reacting a tetramethylpiperidone represented by formula (IIa):

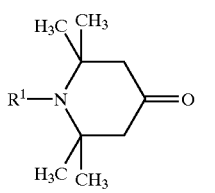

(IIa)

wherein $R^1$ is as defined above, with a diamine represented by formula (IIb):

NH$_2$—R—NH$_2$ (IIb)

wherein R is as defined above, and the diamines have then been refined and purified. Diamines and various methods of their preparation are described in JP-B-58-11454, JP-A-64-50858, and JP-A-5-86029.

Without the isolation and refinement of the dipiperidylamine represented by formula (II), it has heretofore been thought that the polyaminotriazines represented by formula (I) having sufficient properties as stabilizers could not be obtained. However, according to the above-processes, a high yield of the polyaminotriazine represented by formula (I) based on the diamine of formula (IIb) could not be achieved.

SUMMARY AND OBJECTS OF THE INVENTION

The present inventors have conducted studies to develop an effective process for preparing polyaminotriazines and, as a result, discovered novel processes for preparing polyaminotriazines.

Among these is a process in which polyaminotriazines represented by formula (I) can be prepared in a high yield by a polycondensation reaction of a dichlorotriazine represented by formula (III) with the unrefined reaction product of a reduction alkylamination between a tetramethylpiperidone represented by formula (IIa) and a diamine represented by formula (IIb), wherein the diamine represented by formula (II) is not first refined, isolated and purified from the reaction product.

In addition, the present inventors have discovered advantageous conditions for practicing a polycondensation reaction to prepare effectively polyaminotriazines represented by formula (I). In general, polyaminotriazines represented by formula (I) can be prepared by reacting a diamine of represented by formula (II) with a dichlorotriazine represented by the formula (III) in a specified mole ratio of (III)/(II), wherein, in at least 80 mole % of the diamine represented by formula (II), $X^5$ is a piperidyl represented by formula (Ia), in a specified small amount of a water-immiscible aromatic solvent per part of diamine represented by formula (II), in the presence of an inorganic base in a solid, non-aqueous, form under atmospheric pressure at a temperature which is greater than the boiling point of the aromatic solvent while removing, such as by co-distilling off, the water generated in the polycondensation reaction.

The processes of the present invention produce polyaminotriazines represented by formula (I) in high yield.

A process according to the present invention suppresses by-product formation and avoids hydrolysis of the intermediate while achieving a high yield of the polyaminotriazine.

A process according to the present invention can also be conducted in a reaction vessel made of SUS 316L.

The processes according to the present invention can produce polyaminotriazines having an average polymerization degree greater than 6. As a consequence, polyaminotriazines having good properties as stabilizers can be efficaciously prepared according to the present invention.

The processes according to the present invention can produce polyaminotriazines which are not red-brown colored, and which are at least essentially colorless, if not colorless.

DETAILED DESCRIPTION OF THE INVENTION

The present invention provides an improved process for preparing polyaminotriazines represented by formula (I):

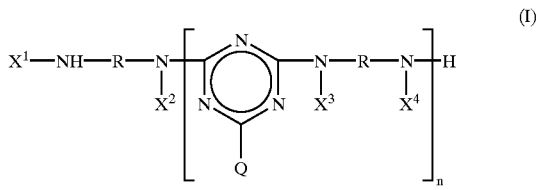

(I)

wherein n is a number from 2 to 20;

$X^1$, $X^2$, $X^3$ and $X^4$, which are same or different, are each hydrogen or piperidyl represented by following formula (Ia):

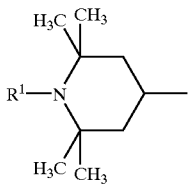

(Ia)

wherein $R^1$ is a hydrogen atom, $C_1$ to $C_{12}$ alkyl, $C_1$ to $C_{18}$ alkoxy, $C_3$ to $C_8$ alkenyl, $C_7$ to $C_{11}$ arylalkyl or $C_3$ to $C_5$ alkenyloxy, wherein at least 75 mole % of $X^1$, $X^2$, $X^3$ and $X^4$ is piperidyl represented by formula (Ia); R is $C_2$ to $C_{12}$ alkylene which can be interrupted by —O— or —$NR^2$—, wherein $R^2$ is hydrogen, $C_1$ to $C_{12}$ alkyl, $C_3$ to $C_{12}$ cycloalkyl or a piperidyl represented by formula (Ia), or R is a divalent $C_6$ to $C_{15}$ cycloaliphatic group; and Q is —$OR^3$, —$NHR^4$ or —$NR^4R^5$, wherein $R^3$ is $C_1$ to $C_{12}$ alkyl, $C_5$ to $C_{12}$ cycloalkyl, benzyl, phenyl, tolyl or piperidyl represented by formula (Ia), $R^4$ is $C_1$ to $C_{12}$ alkyl, $C_3$ to $C_{12}$ alkoxyalkyl, $C_4$ to $C_{12}$ N,N-dialkylaminoalkyl, $C_3$ to $C_5$ alkenyl, phenyl, benzyl, cyclohexyl, tolyl or piperidyl represented by formula (Ia), and $R^5$ is $C_1$ to $C_{12}$ alkyl or cycloalkyl, or $R^4$ and $R^5$, together with the N atom to which they are bonded, form a 5- or 6-membered heterocyclic ring, which comprises conducting a reduction alkylamination of at least one tetramethylpiperidone represented by formula (IIa) with at least one diamine represented by formula (IIb) in the presence of a hydrogenation catalyst; separating out the catalyst, after the completion of the reduction alkylamination reaction, to obtain a crude product (hereinafter, referred to as "crude product (A)"); and then, without refining the crude product (A), e.g. without refining, and isolating and/or purifying a diamine of formula (II) therefrom, conducting a polycondensation reaction between the crude product (A) and at least one dichlorotriazine represented by formula (III) in the presence of an aromatic solvent and an inorganic base.

The polyaminotriazines which can be produced by the processes according to present invention include polyaminotriazines represented by formula (I) wherein $R^1$ is hydrogen or methyl, R is a straight chain or branched chain alkylene having 2 to 12 carbon atoms and Q is —$NHR^4$ or —$NR^4R^5$. In particular, a polyaminotriazine represented by formula (I) wherein $R^1$ is hydrogen, R is hexamethylene, and Q is 1,1,3,3-tetramethylbutylamino is readily obtained by the processes according to the present invention.

Among the tetramethylpiperiodones represented by formula (IIa) are those wherein $R^1$ is hydrogen or lower alkyl, such as methyl, and these are particularly preferred. When $R^1$ in the formula (Ia) or (IIa) is arylalkyl, $R^1$ is, for instance, phenyl alkyl, such as, for example, benzyl, ethyl-phenyl, or butyl-phenyl.

Among the diamines represented by formula (IIb), those wherein R is a straight or branched chain alkylene having 2–12 carbon atoms are preferred, although R is more preferably a straight chain alkylene having from 2–8 carbon atoms. Among these, ethylene or hexamethylene are particularly preferred. The diamine represented by formula (IIb) can, if desired, additionally include 0–20 weight % of water based on the diamine.

The R in the formula (IIb) can also represent at least one divalent cycloaliphatic group having a cycloalkane ring, such as cycloalkylene, methylene dicycloalkylene or cycloalkylene methylene, which may be optionally substituted with an alkyl having up to 12 carbon atoms. The cycloalkylene groups include, among others, cyclopentyl, cyclohexyl, and cycloheptyl. The methylene dicycloalkylene groups include, among others, methylene dicyclopentyl, metheylene dicyclohexyl, and methylene dicycloheptyl. The cycloalkylene methylene groups include, among others, cyclopentyl methylene, cyclohexyl methylene and cycloheptyl methylene.

When Q is —$NHR^4$, $R^4$ is preferably a straight or branched chain alkyl having 4–8 carbon atoms. When Q is —$NHR^4$, 1,1,3,3,-tetramethylbutylamino is preferred. When Q is —$NR^4R^5$ which forms a 5- or 6-membered heterocyclic ring, Q includes, for instance, 1-pyrrolidinyl, 1-imidazolidinyl, piperidino, 1-piperazinyl or morpholino, among which morpholino is preferred. The present processes can produce a polyaminotriazine in which the n repeating units may be the same or different, and thus, for instance, Q may be the same or different between the n repeating units.

The polyaminotriazines obtained according to the present processes include those wherein n is 2 to 20. The present processes can produce a mixture of polyaminotriazines wherein n has an average value of at least 6, and, in particular wherein n has an average value of about 7 to about 11. These latter polyaminotriazines are particularly useful as stabilizers in polymer compositions.

Tetramethylpiperiodones represented by formula (IIa) and diamines represented by formula (IIb) are commercial products and are readily available to those skilled in the art.

The reduction alkylamination is conducted in the presence of hydrogen and a hydrogenation catalyst. Useful hydrogenation catalysts include, among others, platinum, nickel, cobalt and palladium. By preference, the catalyst is a supported on an inert carrier, such as platinum or palladium supported on carbon (hereinafter described as platinum/carbon or palladium/carbon, respectively), or Raney nickel.

When the hydrogenation catalyst is platinum or palladium, the amount of the catalyst present is from 0.001 to 0.04 weight % based on the tetramethylpiperidone represented by formula (IIa) and the reaction temperature is from about 40° C. to about 140° C. When the hydrogenation catalyst is Raney nickel, the amount of the catalyst present is from 0.1 to 30 weight % based on the tetramethylpiperidone represented by formula (IIa) and the reaction temperature is from about 100° C. to about 180° C.

The amount of the tetramethylpiperiodone of represented by formula (IIa) is preferably at least 1.5 moles but less than 2.1 moles, and particularly is from at least 1.7 to 1.95 moles, relative to the amount of the diamine represented by formula (IIb). If 2.1 moles or more of a tetramethylpiperiodone represented by formula (IIa) are used in the reaction, and the resulting product is used in the polycondensation with a dicholorotriazine represented by formula (III) without refining the resulting product, the polyaminotriazine(s) thus obtained is often colored in red-brown. If the amount of the tetramethylpiperidone represented by formula (IIa) is too low, such as less than 1.5 moles, the polyaminotrazines obtained exhibit insufficient stabilizing effects in organic materials. Using 1.5 moles or more of the tetramethylpiperidone represented by formula (IIa) per 1.0 mole of the diamine represented by formula (IIb) in the reduction alkylamination, polyaminotriazines represented by formula (I) wherein 75 mole % or more of $X^1$, $X^2$, $X^3$ and $X^H$ is piperidyl represented by formula (Ia) can be obtained.

The reduction alkylamination of a tetramethylpiperidone represented by formula (IIa) with a diamine represented by formula (IIb) can be conducted in a manner known to those skilled in the art. For example, the reduction alkylamination can be conducted in the presence of hydrogen and platinum, palladium or Raney nickel, and using a lower-alkyl alcohol, such as methanol, ethanol, propanol, or a mixture of the alcohol and water, as the solvent. Conducting the reaction in this manner yields only a small amount of by-products other than monopiperidyl compounds, and the resulting crude product can be polycondensed with a dichlorotriazine represented by formula (III) after just filtering off the catalyst and distilling off the solvent. In general, this procedure is therefore preferred. For instance, similar to that described in JP-A-58-11454, the reaction can be conducted in methanol in the presence of a platinum/carbon or palladium/carbon catalyst at 55° C. to 75° C. under a hydrogen pressure of 9 to 10 atm. for 4 to 5 hours.

Another suitable and preferred reduction alkylamination is similar to that described in JP-A-56-86029 and EP-A1-508940. A reaction between a tetramethylpiperidone represented by formula (IIa) and a diamine represented by formula (IIb) can be conducted at 50° C. to 100° C. in the absence of solvent while distilling off water from the reaction mixture under a reduced pressure, such as 1–135 Torr. Next, a reduction alkylamination of the resulting product with hydrogen can be carried out in the presence of a platinum, palladium or Raney nickel catalyst to obtain a crude product. The catalyst can, if desired, be supported on an inert carrier such as carbon or silica. According to JP-A-56-86029 and EP-A1-508940 the catalyst is removed, and the crude product is then refined to remove light fractions to obtain a refined product. However, as stated hereinabove, in the present invention, a refined product is not required. More particularly, a reaction between a tetramethylpiperidone represented by formula (IIa) and a diamine represented by formula (IIb) can be conducted, first, at 50° C. to 60° C. for 1 hour without using solvent and, then, at 60° C. under reduced pressure, such as 30 Torr, for 3 hours, while distilling off water, and thereafter, a reduction alkylamination can then be conducted with hydrogen in the presence of either platinum/carbon or palladium/carbon at 90° C. at a hydrogen pressure of 5 atm. for 4 hours or in the presence of decanted Raney nickel at 100° C. at a hydrogen pressure of 100 atm. for 4 hours.

The crude product (A) mainly contains diamines represented by formula (II). In principle, the crude product (A) consists essentially of diamines represented by formula (II). For purposes of process A, a crude product (A) is desirably water-free. The crude product contains less than 1 weight % of by-products such as N-(2-propyl)-$N^1$-(2,2,6,6-tetramethyl-4-piperidyl)hexamethylenediamine, if a refined and purified tetramethylpiperidone represented by formula (IIa), such as one having a high purity of 99 weight % or more, which was obtained following distillation, recrystallization or the like, is used. The small amount of potential by-product contamination does not have any effect on the stabilizing properties of the polyaminotriazines produced.

The dichlorotriazines represented by formula (III) can be prepared according to a known process, such as described in JP-A-52-71486, in which dichlorotriazines are prepared by reacting a cyanuric trichloride and a monofunctional compound of the formula —QH, wherein Q is as mentioned above. The resulting reaction solution can be used in the process of the present invention without isolating (purifying) the dichlorotriazines represented by formula (III), and is preferred. However, the dichlorotriazines represented by formula (III) which have been isolated (purified) from the resulting reaction solution by known methods, such as recrystallization, can also, if desired, be used in the present invention.

Preferred examples of the dichlorotriazines represented by formula (III) include 2,4-dichloro-6-(1,1,3,3-tetramethylbutylamino)-1,3,5-triazine and 2,4-dichloro-6-morpholino-1,3,5-triazine.

The polycondensation degree of polyaminotriazines represented by formula (I) can be varied as a function of the amount of the dichlorotriazine represented by formula (III) used in the polycondensation reaction. In general, a preferred amount of the dichlorotriazine represented by formula (III) is usually 0.75 to about 1 mole, and particularly from 0.8 to 0.9 mole, based on 1 mole of the diamine of the formula (IIb). If the amount is less than 0.75 mole, polyaminotriazines having a low polycondensation degree, such as in formula (I) wherein n has a value less than 5, are obtained. If the amount exceeds about 1 mole, the polycondensation does not proceed to completion.

In the polycondensation reaction, a solid inorganic base or aqueous solution thereof can be used, although in the Process A embodiment the inorganic base is a solid, such as a non-hydrated solid, and not an aqueous solution. Among the preferred classes of inorganic bases are alkali metal hydroxides, such as sodium hydroxide or potassium hydroxide, and alkali metal carbonates, such as sodium carbonate or potassium carbonate. Particularly preferred is sodium hydroxide or potassium hydroxide. By preference the amount of the inorganic base used in the polycondensation reaction is 2 to 3 equivalents, and more preferably 2.2 to 2.5 equivalents, per 1 equivalent of the dichlorotriazine represented by formula (III). If the amount is less than 2 equivalents, the polycondensation hardly proceeds to completion. An amount exceeding 3 equivalents is disadvantageous from the economical view.

If an organic base such as triethylamine is used in the polycondensation reaction, only polyaminotriazines having a relatively low polycondensation degree (n in the formula (I) is a value less than 6) are obtained and only in low yield.

The present processes can be conducted in the presence of at least one aromatic solvent. These solvents are water-immiscible and inert to the polycondensation reaction. Aromatic solvents include, for instance, xylene, ethylbenzene, toluene, o-dichlorobenzene and mesitylene. If a solvent having the boiling point higher than 170° C. under atmospheric pressure such as o-dichlorobenzene is used, high temperature and/or high vacuum is required in order to remove the solvent from the reaction mixture. Therefore, aromatic solvents having a relatively low boiling point are preferred, such as a boiling point of about 100° C. to 160° C. under atmospheric pressure. These lower-boiling aromatic solvents include xylene, ethylbenzene, toluene or mixtures thereof, of which xylene, ethylbenzene or a mixture of xylene and ethylbenzene are particularly preferred. For smooth operation, 0.1 weight part or more of solvent per 1 weight part of the crude product (A) is usually required.

The polycondensation reaction can proceed at a temperature of at least about 80° C., although in general the reaction temperature should be in a range of from 145° C. to 220° C. and preferably from 155° C. to 190° C. when the reaction is carried out under an elevated pressure. When the reaction is carried out under atmospheric pressure, a preferable reaction temperature range is from 145° C. to 190° C. which ensures more ready control over the reaction. If the reaction temperature is lower than 145° C., a number of disadvantageous results can occur, including a need for a long reaction time and a reduced polycondensation degree, as well as increased production of by-products, and/or a reduced yield. If the reaction temperature exceeds 220° C., the starting materials and the reaction products are often decomposed.

The polycondensation reaction can be carried out in various manners. For example, the inorganic base, crude product (A) and the dichlorotriazine represented by formula (III) can be mixed (stirred together etc.) at room temperature and, then, the reaction temperature can be raised to a specific temperature (or within a selected temperature range) which can be maintained during the polycondensation. However, in order to suppress by-product formation and to improve the yield, the dichlorotriazine represented by formula (III) is preferably added, such as by metering, to a solution of crude product (A) (such as in the inert water-immiscible aromatic solvent) in which the inorganic base has been dispersed, at the specific reaction temperature. The dichlorotriazine represented by formula (III) can, if desired, be obtained by allowing a cyanuric trichloride and a monofunctional compound of the formula —QH in an appropriate solvent, such as an aromatic solvent useful in the polycondensation step, to react, and isolating the dichlorotriazine therefrom. The isolated dichlorotriazine can be used in the polycondensation reaction, although it is preferred that a reaction mixture is used without isolating the resulting dichlorotriazine. The polycondensation reaction can be carried out either under an elevated pressure or under atmospheric pressure.

If the polycondensation reaction is carried out at elevated pressure, a reaction temperature suitable for the polycondensation can be readily achieved regardless of the amount of the aromatic solvent by using an autoclave. With an autoclave, it is preferred to use the inorganic base as a concentrated aqueous solution. For example, the polyaminotriazines represented by formula (I) can be prepared by slowly adding, e.g. metering, a solution of the dichlorotriazine represented by formula (III) in an aromatic solvent dropwise to a mixture of the crude product (A) and 50% aqueous solution of sodium hydroxide or potassium hydroxide in an autoclave while maintaining the temperature in a range from 145° C. to 220° C. to carry out the polycondensation reaction under an elevated pressure.

If the polycondensation reaction is carried out under atmospheric pressure, a reaction temperature suitable for the reaction can be maintained by distilling off water, such as the water generated in the reaction, and, if necessary, a part of the solvent from the reaction system, while controllably adding the solution of the dichlorotriazine represented by formula (III). However, in general a very small amount of the solvent must be used in order to attain a reaction temperature greater than 190° C., and the workability is not good. On the other hand, the higher reaction temperature is preferred in order to achieve high yield and a higher polycondensation degree. Therefore, under atmospheric pressure, it is generally preferred to carry out the polycondensation reaction at a temperature of 145° C. to 190° C., and preferably 155° C. to 180° C., in the presence of 0.1 to 1 weight part, and preferably 0.2 to 0.8 weight part, of solvent per 1 weight part of the crude product (A).

If the polycondensation reaction is carried out under atmospheric pressure, the inorganic base should be used in a solid form, and not in solution. Examples of preferred solid inorganic bases include particules, such as a powder or flake, of sodium hydroxide or potassium hydroxide. In particular, solid sodium hydroxide is preferred. The solid inorganic base can, if desired, be used in the form of a suspension in an inert solvent, such as a water immiscible aromatic solvent compatible with the polycondensation. Such additional solvent should be accounted for in achieving the desired conditions for conducting the polycondensation reaction, such as in determinining the relative amount of solvent present.

The suitable amount of the solvent, i.e., 0.1 to 1 weight part based on 1 weight part of the crude product (A), can be achieved at the completion of the addition of the dichlorotriazine represented by formula (III) by adding the dichlorotriazine slowly and dropwise over a long period and by distilling off water and, if necessary, a part of the solvent from the reaction system. The suitable amount, i.e., 0.1 to 1 weight part per 1 weight part of the crude product (A), can be achieved by the start of the main stage of the polycondensation reaction to obtain the preferable results. For instance, as described in Example 1(c), by controlling the rate at which a solution of the dichlorotriazine in the aromatic solvent is being added to the crude product (A), and the amount of aromatic solvent being distilled off, the temperature is maintainable within the desired range while also ensuring that upon completion of the addition that the desired amount of aromatic solvent relative to the crude product (A) remains as the main stage of polycondensation reaction is thereafter allowed to proceed until completion while removing, such as by distilling off, the water of reaction. The distillation of solvent can, if necessary, be allowed to continue subsequent to the addition of the dichlorotriazine solution for a sufficient period of time to ensure attainment of the desired aromatic solvent amount. Therefore, a solution of the dichlorotriazine represented by formula (III) containing more than 1 weight part of the solvent per 1 weight part of the crude product (A) can be used to obtain the preferable results as long as the condition of 0.1 to 1 weight part is achieved by distilling off a part of the solvent.

Another improved process embodiment for preparing polyaminotriazines represented by formula (I) comprises reacting, e.g. polycondensing, a diamine of represented by formula (II) with a dichlorotriazine represented by formula (III) in a mole ratio (III)/(II) of 0.83 to 0.98, wherein, in at least 80 mole % of the diamine represented by formula (II), $X^5$ is a piperidyl of represented by formula (Ia), wherein the reaction is conducted in 0.1 to 1 weight part of at least one water-immiscible aromatic solvent per 1 part of diamine represented by formula (II) and in the presence of an inorganic base in a solid (e.g. non-aqueous) form at atmospheric pressure and at a temperature greater than the boiling point of the aromatic solvent while removing, such as by co-distilling off, water generated in the reaction. (Hereinafter, this process is referred to as Process A). carrying out, e.g. effecting, the reaction under atmospheric pressure in the presence of a small amount of aromatic solvent at a temperature greater than the boiling point of the aromatic solvent while removing, such as by co-distilling off, water generated in the reaction and while using a non-aqueous solid inorganic base is a salient characteristic of this process.

According to Process A, by-product formation and hydrolysis of the intermediate are suppressed and a high yield of the polyaminotriazine is realized. In addition, the process can be conducted in a reaction vessel made of SUS 316L.

The crude product (A) can be used as the diamine represented by formula (II) in Process A. The advantages of this process can also be achieved, even when using a diamine represented by formula (II) which has been refined and isolated by a known methods, such as distillation or recrystallization. If refined, isolated and purified diamines are used, less colored polyaminotriazines is obtained. Therefore, in order to reduce the color of the product, using a refined and isolated diamine is preferred. Diamines represented by formula (II) prepared by mixing an isolated diamine wherein $X^5$ is hydrogen and an isolated diamine where $X^5$ is piperidyl at desired proportion can also be used and the advantages of Process A can be achieved. For instance, this technique can be used to obtain the diamines represented by formula (II) of which at least 80 mole % have $X^5$ represented by the formula of (Ia).

In the Process A embodiment, diamines represented by formula (II) wherein R is a straight or branched chain alkylene having 2–12 carbon atoms are preferred, although R is more preferably a straight chain alkylene having 2–8 carbon atoms. In particular, R is preferably ethylene or hexamethylenediamine. $R^1$ in the formula (Ia) is preferably hydrogen or lower alkyl, such as methyl.

To prepare polyaminotriazines represented by formula (I) wherein 75 mole % or more of $X^1$, $X^2$, $X^3$ and $X^4$ is piperidyl is represented by formula (Ia), $X^5$ must be piperidyl represented by formula (Ia) in at least 80 mole % of the diamine represented by formula (II). If less than this 80 mole % is used, 15 polyaminotriazines which exhibit inferior properties as stabilizers for synthetic resins are liable to be produced.

The preferred diamines represented by formula (II) which are useful in Process A include:

N,N'-bis(2,2,6,6-tetramethyl-4-piperidyl)hexamethylenediamine,

N,N'-bis (1,2,2,6,6-pentamethyl-4-piperidyl)hexamethylenediamine, a mixture of N-(2,2,6,6-tetramethyl-4-piperidyl)hexamethylenediamine and N,N'-bis (2,2,6,6-tetramethyl-4-piperidyl)hexamethylenediamine, and a mixture of N-(1,2,2,6,6-pentamethyl-4-piperidyl) hexamethylenediamine and N,N'-bis (1,2,2,6,6-pentamethyl-4-piperidyl)hexamethylenediamine.

Atmospheric pressure includes such a pressure which is easily attained without special manipulation such as compressing or decompressing.

In order to achieve the advantages of Process A, the ratio of the dichlorotriazine represented by formula (II) to the diamine represented by formula (II) should be from 0.83 to 0.98, the reaction temperature must be higher than the boiling point of the aromatic solvent, and the inorganic base must be used in a solid form. If an aqueous solution of the inorganic base is used, a reaction temperature higher than the boiling point of the aromatic solvent can hardly be achieved.

The following illustrates a preferred means for carrying out Process A. The polycondensation reaction is carried out by slowly adding a solution of the dichlorotriazine represented by formula (III). in an inert water-immiscible aromatic solvent to a mixture of the diamine represented by formula (II) and sodium hydroxide or potassium hydroxide which is kept at a temperature higher than the boiling point of the aromatic solvent while distilling off water generated in the reaction and a part of the aromatic solvent.

After the completion of the polycondensation, the reaction mixture is washed with water, dried and filtered. The filtration can be accelerated by adding a filter aid, such as cellulose, diatomaceous earth and fuller's earth. By evaporating solvent from the filtrate, the polyaminotriazines represented by formula (I) are obtained in a solid mass, which can be crushed, if necessary.

Examples of the polyaminotriazines represented by formula (I) which can be obtained effectively according to the present invention include:

a polycondensate of 2,4-dichloro-6-(1,1,3,3-tetramethylbutylamino)-1,3,5-triazine with a mixture of N-(2,2,6,6-tetramethyl-4-piperidyl)hexamethylenediamine and N,N'-bis(2,2,6,6-tetramethyl-4-piperidyl)hexamethylenediamine, a polycondensate of 2,4-dichloro-6-morpholino-1,3,5-triazine with a mixture of N-(2,2,6,6-tetramethyl-4-piperidyl)hexamethylenediamine and N,N'-bis(2,2,6,6-tetramethyl-4-piperidyl)hexamethylenediamine, a polycondensate of 2,4-dichloro-6-(1,1,3,3-tetramethylbutylamino)-1,3,5-triazine with a mixture of N-(1,2,2,6,6-pentamethyl -4-piperidyl) hexamethylenediamine and N,N'-bis (1,2,2,6,6-pentamethyl-4-piperidyl)hexamethylenediamine, and a polycondensate of 2,4-dichloro-6-morpholino)-1,3,5-triazine with a mixture of N-(1,2,2,6,6-pentamethyl-4-piperidyl) hexamethylenediamine and N,N'-bis(1,2,2,6,6-pentamethyl-4-piperidyl)hexamethylenediamine.

If an isolated diamine(s) is used in the present invention, preferred polycondensates include:

a polycondensate of 2,4-dichloro-6-(1,1,3,3-tetramethylbutylamino)-1,3,5-triazine with N,N'-bis(2,2,6,6-tetramethyl-4-piperidyl)hexamethylenediamine, a polycondensate of 2,4-dichloro-6-morpholino-1,3,5-triazine with N,N'-bis(2,2,6,6-tetramethyl-4-piperidyl)hexamethylenediamine, a polycondensate of 2,4-dichloro-6-(1,1,3,3-tetramethylbutylamino)-1,3,5-triazine with N,N'-bis(1,2,2,6,6-pentamethyl-4-piperidyl)hexamethylenediamine, and a polycondensate of 2,4-dichloro-6-morpholino)-1,3,5-triazine with N,N'-bis(1,2,2,6,6-pentamethyl-4-piperidyl)hexamethylenediamine.

According to the processes of the present invention, polyaminotriazines represented by formula (I) having sufficient properties as stabilizers can be obtained in a high yield.

Processes for preparing polyaminotriazines are described in U.S. Pat. Nos. 4,086,204, 4,492,791, 4,104,248, Japanese application 5-329084 filed Dec. 24, 1993, Japanese Application 6-151221, field Jul. 1, 1994, and Japanese Application 6-151220 filed Jul. 1, 1994, the complete disclosures of which are incorporated herein by reference.

The following examples illustrate the present invention in more detail. They are illustrative and should not be interpreted as to limit the present invention. In the examples, "%" means "weight %", unless otherwise mentioned.

EXAMPLE 1

(a) Preparation of Intermediate

Into an autoclave, 94.6 grams (0.609 mole) of 2,2,6,6-tetramethyl-4-piperidone, 37.3 grams (0.321 mole) of hexamethylenediamine, 200 grams of methanol and 0.55 gram of 5% platinum/carbon were charged and the mixture was kept at 65° C. under hydrogen at a pressure of 9 to 10 atmospheres for 3 hours and thereafter the temperature was maintained at 70° C. for 1 hour. (The molar ratio of 2,2,6,6-tetramethyl-4-piperidone to hexamethylenediamine was 1.9/1.0) After the reaction was completed, the catalyst was filtered off and the methanol was distilled off under reduced pressure to obtain 119.7 grams of a concentrated mass. According to an analysis with gas-chromatography, the concentrated mass thus obtained contained 94.4% of N,N'-bis(2,2,6,6-tetramethyl-4-piperidyl)hexamethylenediamine and 5.4% of N-(2,2,6,6-tetramethyl-4-piperidyl)hexamethylenediamine.

(b) Preparation of Dichlorotriazine

Into a flask, 20 grams of water, 52.3 grams (0.284 mole) of cyanuric chloride and 130 grams of mixed xylenes having a boiling point of 138–141° C. were charged, and 37.5 grams (0.290 mole) of 1,1,3,3-tetramethylbutylamine was slowly and dropwise added into the mixture while maintaining the temperature at 8–10° C. Then, 57.9 grams of 20% aqueous hydroxide solution was slowly and dropwise added into the mixture while keeping the temperature at 8–10° C. After the reaction was complete, the oil (organic) and water phases were separated and the water phase was removed to obtain a xylene solution of 2,4-dichloro-6-(1,1,3,3-tetramethylbutylamino)-1,3,5-triazine, (c) Preparation of Polyaminotriazine Into a 500 ml four necked flask equipped with a dean-stark trap, all the concentrated mass obtained in Example 1(a) and 28.4 grams (0.71 mole) of sodium hydroxide powder were charged to obtain a mixture, and the temperature of the mixture was raised to 160° C. Then, into the mixture, the xylene solution of 2,4-dichloro-6(1,1,3,3-tetramethylbutylamino)-1,3,5-triazine obtained in (b) was dropwise added over 4 hours. After the dropwise addition was started, the water generated in the reaction started to reflux. The refluxing water was distilled off. After a while, xylene also started to reflux. As the dropwise addition was continued, the reaction temperature started to decrease. In order to keep the reaction temperature at 160° C. or higher, a part of the refluxing xylene was distilled off. At the end of addition of the solution, the total amount of the xylene distilled off was 88 grams, which means that, at the end of the dropwise addition, the xylene content in the mixture was 0.35 weight part per 1 weight part of the concentrated mass from Example 1(a). After the end of the dropwise addition of the solution, the reaction temperature was maintained at 160° C. for 5 hours while the water generated in the reaction was distilled off. After the reaction was completed, water was added to the reaction mass in order to dissolve the sodium chloride generated in the reaction, and water and sodium chloride were separated off. The resulting xylene solution (liquid reaction mass containing remaining xylene) was filtered to remove by-products and concentrated to obtain a product. Then, the resulting product was cooled to obtain 166.3 grams of solid resin, which was crushed.

Yield 92%

Number average molecular weight 4900 n=7.5

(From Example 1 to 7, yields are based on the amount of diamine used for the reaction in (a).)

EXAMPLE 2

(a) Preparation of Intermediate

Example 1(a) was repeated, except that the reaction condition of "at 65° C. for 3 hours" was changed to "at 60° C. for 3.5 hours" to obtain 120.1 grams of concentrated mass. The concentrated mass thus obtained contained 87.0% of N,N'-bis(2,2,6,6-tetramethyl-4-piperidyl) hexamethylenediamine and 12.1 % of N-(2,2,6,6-tetramethyl-4-piperidyl)hexamethylenediamine.

(b) Preparation of Dichlorotriazine

Example 1(b) was repeated to obtain a xylene solution of 2,4-dichloro-6-(1,1,3,3-tetramethylbutylamino)-1,3,5-triazine.

(c) Preparation of Polyaminotriazine

Example 1(c) was repeated, except that the concentrated mass and xylene solution of 2,4-dichloro-6-(1,1,3,3-tetramethylbutylamino)-1,3,5-triazine obtained in Example 1 was replaced by those obtained in Examples 2(a) and (b), respectively, to obtain 164.7 grams of a solid resin, which was then crushed.

At the end of addition of the solution, the total amount of the xylene distilled off was 87 grams, which means that, at the end of the addition, the xylene content in the mixture was 0.36 weight part per 1 weight part of the concentrated mass from Example 2(a).

Yield 91%

Number average molecular weight 4400 n=6.7

EXAMPLE 3

(a) Preparation of Intermediate

Example 1(a) was repeated, except that the reaction temperature (65° C.) and amount of 2,2,6,6-tetramethyl-4-piperidone (94.6 g, 0.609 mole) were changed to 59° C. and 89.6 grams (0.577 mole), respectively, to obtain 115.3 grams of a concentrated mass. (The molar ratio of 2,2,6,6-tetramethyl-4-piperidone to hexamethylenediamine was 1.8/1). The concentrated mass thus obtained contained 80.3% of N,N'-bis(2,2,6,6-tetramethyl-4-piperidyl) hexamethylenediamine and 19.4% of N-(2,2,6,6-tetramethyl-4-piperidyl) hexamethylenediamine.

(b) Preparation of Dichiorotriazine

Into a flask, 20 grams of water, 50.0 grams (0.271 mole) of cyanuric chloride and 125 grams of a mixed xylene were charged and 35.9 grams (0.278 mole) of 1,1,3,3-tetramethylbutylamine was slowly and dropwise added into the mixture while keeping the temperature at 8–10° C. Then, 55.5 grams of a 20% aqueous hydroxide solution was slowly and dropwise added into the mixture while keeping the temperature at 8–10C. After the reaction was complete, the oil (organic) and water phases were separated and the water phase was separated off to obtain a xylene solution of 2,4-dichloro-6-(1,1,3,3-tetramethylbutylamino)-1,3,5-triazine.

(c) Preparation of Polyaminotriazine

Example 1(c) was repeated, except that the concentrated mass and the xylene solution of 2,4-dichloro-6-(1,1,3,3-tetramethylbutylamino)-1,3,5-triazine obtained in Example 1 were replaced by those obtained in Examples 3(a) and (b), respectively, and the amount of sodium hydroxide powder (28.4 grams, 0.71 mole) was changed to 27.2 grams (0.68 mole) to obtain 161.7 g of a solid resin, which was then crushed.

At the end of the dropwise addition of the xylene solution, the total amount of the xylene distilled off was 85 grams, which means that, at the end of the addition, the xylene content in the mixture was 0.35 weight part per 1 weight part of the concentrated mass from Example 3(a).

Yield 93%

Number average molecular weight 3700 n=5.5

EXAMPLE 4

(a) Preparation of Intermediate

Example 1(a) was repeated, except that the reaction temperature (65° C.) and the amount of 2,2,6,6-tetramethyl-4-piperidone (94.6 grams, 0.609 mole) were changed to 60° C. and 93.6 grams (0.603 mole), respectively, to obtain 119.4 grams of a concentrated mass. (The molar ratio of 2,2,6,6-tetramethyl-4-piperidone to hexamethylenediamine was 1.88/1). The mass thus obtained contained 94.6% of N,N'-bis(2,2,6,6-tetramethyl-4-piperidyl) hexamethylenediamine and 4.8% of N-(2,2,6,6-tetramethyl-4-piperidyl)hexamethylenediamine.

(b) Preparation of Dichlorotriazine

Example 1(b) was repeated to obtain a xylene solution of 2,4-dichloro-6-(1,1,3,3-tetramethylbutylamino)-1,3,5-triazine.

(c) Preparation of Polyaminotriazine

Into an autoclave, all of the concentrated mass obtained in Example 4(a) and 56 grams of 50% aqueous sodium hydroxide solution were charged to obtain a mixture, and the temperature of the mixture was raised to 180° C. Then, into the mixture, the xylene solution of 2,4-dichloro-6-(1,1,3,3-tetramethylbutylamino)-1,3,5-triazine obtained in Example 4(b) was dropwise added over 4 hours. After the dropwise addition was started, an increase in inner temperature was observed and, after a while, an increase in pressure was also observed. After the end of the dropwise addition of the solution, the reaction temperature was maintained at 180° C. for 5 hours. After the reaction was completed, a water phase containing sodium chloride solution generated in the reaction was removed. The resulting xylene solution was filtered to remove by-products and concentrated to obtain a product. The resulting product was cooled to obtain 165.6 grams of a solid resin, which was then crushed.

Yield 92%

Number average molecular weight 4700 n=7.2

EXAMPLE 5

(a) Preparation of Intermediate

Into a flask, 92.2 grams (0.594 mole) of 2,2,6,6-tetramethyl-4-piperidone and 37.3 grams (0.321 mole) of hexamethylenediamine were charged to form a mixture. The mixture was maintained at 50–60° C. for one hour, and then water was removed at 60° C. under reduced pressure (30 Torr) for 3 hours. The resulting reaction mass and 0.55 gram of 5% platinum/carbon were charged in an autoclave and, then, that mixture was maintained at 90° C. under hydrogen at a pressure of 5 atmospheres for 4 hours. (The molar ratio of 2,2,6,6-tetramethyl-4-piperidone to hexamethylenediamine was 1.85/1). After the reaction was completed, the catalyst was filtered off to obtain 121.9 grams of reaction product. The reaction product thus obtained contained 92.2% of N,N'-bis(2,2,6,6-tetramethyl-4-piperidyl) hexamethylenediamine and 7.5% of N-(2,2,6,6-tetramethyl-4-piperidyl) hexamethylenediamine.

(b) Preparation of Dichlorotriazine

Example 1(b) was repeated to obtain a xylene solution of 2,4-dichloro-6-(1,1,3,3-tetramethylbutylamino)-1,3,5-triazine.

(c) Preparation of Polyaminotriazine

Example 4(c) was repeated, except that the concentrated mass obtained in Example 4(a) was replaced by all of the reaction product obtained in Example 5(a) to obtain 162.3 grams of a solid resin, which was then crushed.

Yield 91%

Number average molecular weight 4800 n=7.0

EXAMPLE 6

(a) Preparation of Intermediate

Example 5(a) was repeated, except that the amount of 2,2,6,6-tetramethyl-4-piperidone of (92.2 grams, 0.594 mole) was changed to 94.7 grams (0.610 mole), to obtain 121.0 grams of reaction product. (The molar ratio of 2,2,6,6-tetramethyl-4-piperidone to hexamethylenediamine was 1.9/1). The reaction product thus obtained contained 95.1% of N,N'-bis(2,2,6,6-tetramethyl-4-piperidyl) hexamethylenediamine and 4.5% of N-(2,2,6,6-tetramethyl-4-piperidyl)hexamethylenediamine.

(b) Preparation of Dichlorotriazine

Example 1(b) was repeated to obtain a xylene solution of 2,4-dichloro-6-(1,1,3,3-tetramethylbutylamino)-1,3,5-triazine.

(c) Preparation of Polyaminotriazine

Example 1(c) was repeated, except that the concentrated mass and the xylene solution of 2,4-dichloro-6-(1,1,3,3-tetramethylbutylamino)-1,3,5-triazine obtained in Example 1 were replaced by those obtained in Examples 6(a) and (b), respectively, to obtain 168.4 grams of a solid resin, which was then crushed.

At the end of addition of the xylene solution, the total amount of the xylene distilled off was 89 grams, which means that, at the end of the addition, the xylene content in the mixture was 0.34 weight part per 1 weight part of the concentrated mass from Example 6(a).

Yield 93%

Number average molecular weight 4700 n=7.2

EXAMPLE 7

(a) Preparation of Intermediate

Example 1(a) was repeated, except that the reaction temperature (65° C.), and the amount of 2,2,6,6-tetramethyl-4-piperidone (94.6 grams, 0.609 mole) were changed to 61° C. and 104.6 grams (0.674 mole), respectively, to obtain 129.1 grams of a concentrated mass. (The molar ratio of 2,2,6,6-tetramethyl-4-piperidone to hexamethylenediamine was 2.1/1). The concentrated mass thus obtained contained 97.6% of N,N'-bis(2,2,6,6-tetramethyl-4-piperidyl) hexamethylenediamine and 2.0% of 2,2,6,6-tetramethyl-4-piperidone, but N-(2,2,6,6-tetramethyl-4-piperidyl) hexamethylenediamine was not detected.

(b) Preparation of Dichlorotriazine

Example 1(b) was repeated, except that the amounts of cyanuric chloride, mixed xylene, 1,1,3,3-tetramethylbutylamine and 20% aqueous hydroxide solution were changed to 53.0 grams (0.287 mole), 132 grams, 38.0 grams (0.294 mole) and 58.8 grams, respectively, to obtain a xylene solution of 2,4-dichloro-6-(1,1,3,3-tetramethylbutylamino)-1,3,5-triazine.

(c) Preparation of Polyaminotriazine

Example 1(c) was repeated, except that the concentrated mass and the xylene solution of 2,4-dichloro-6(1,1,3,3-tetramethylbutylamino)-1,3,5-triazine obtained in Example 1 were replaced by those obtained in Examples 7(a) and (b), respectively, and the amount of sodium hydroxide powder (28.4 grams, 0.71 mole) was changed to 28.8 grams (0.72 mole) to obtain 175.9 grams of a solid resin, which was then crushed.

At the end of addition of the xylene solution, total amount of the xylene distilled off was 88 grams, which means that, at the end of the addition, xylene content in the mixture was 0.34 weight part per 1 weight part of the concentrated mass from Example 7(a).

Yield 92%

Number average molecular weight 7200 n=11.4

Reference Example 1

Degree of coloration of Polyaminotriazine

The light transmittance of solutions of polyaminotriazines obtained in Examples 1–7 was measured, according to the measuring conditions mentioned below. Light transmittance is inversely related to the "transparency" of the polyaminotriazine. Thus, the higher the light transmittance is, the more colorless and transparent the polyaminotriazine.

Measuring Conditions (1) Preparation of the Samples 1.0 gram of polyaminotriazines obtained in each of Examples 1–7 was dissolved in 10 ml of toluene and was filtered with a membrane filter.

(2) Apparatus Used for the Measuring

U-3400 type Spectrometer (manufactured by Hitachi Co., Ltd.)

Measuring wave length: 300–600 nm

Scan speed: 120 nm/min.

TABLE 1

| | Light Transmittance (%) | | |
|---|---|---|---|
| Example No. | 350 nm | 400 nm | 450 nm |
| 1 | 38.06 | 73.01 | 89.24 |
| 2 | 68.57 | 89.15 | 95.52 |
| 3 | 62.75 | 86.70 | 95.46 |
| 4 | 26.90 | 78.76 | 91.90 |
| 5 | 66.24 | 88.72 | 94.58 |
| 6 | 53.91 | 89.79 | 98.23 |
| 7 | 16.10 | 55.65 | 83.86 |

Reference Example 2

The compounding ingredients shown below in Table II were dry-blended with an unstablized linear low density polyethylene (LLDPE) to prepare two mixtures.

TABLE II

| Compounding Composition | |
|---|---|
| Unstablized LLDPE | 100 parts |
| Calcium stearate | 0.1 part |
| * 1 | 0.1 part |
| * 2 | 0.08 part |
| Test stabilizer * 3 | 0.1 part |

* 1: n-Octadecyl 3-(3,5-di-tert-butyl-4-hydroxyphenyl) propionate
* 2: Tetrakis (2,4-di-tert-butylphenyl)-4,4' biphenylene phosphonite
* 3: one mixture contained a test stabilizer as obtained in Example 6, and the other mixture contained a test stabilizer as obtained in Example 10

Each of the two dry-blended mixtures was melt-kneaded by using a 30 mm φ monoaxial extruder at 210° C. and injected from T-die to form a film with thickness of 20±2 μm. Each film was punched to. obtain a test piece. Each test piece was put in a sunshine weather-o-meter and irradiated with light under the following conditions: light source: carbon arc, black panel temperature: 83° C., and water spray time of 18 minutes per 120 minutes cycle. When the stabilizer obtained in Example 6 was used, it took 600 hours until the test piece became unable to be stretched more than 50%. When the stabilizer obtained in Example 10 was used, it took 610 hours until the test piece was unable to be stretched more than 50%. These results show that the polyaminotriazine obtained in Example 6, wherein an unrefined crude product (A) was used as the diamine represented by formula (II), has sufficient stabilizing effect as a stabilizer, and exhibits almost the same stabilizing effect as the polyaminotriazine obtained in Example 10, wherein a refined diamine represented by (II) was used.

EXAMPLE 8

Into a 500 ml four necked flask equipped with a dean stark trap, 84.5 grams (0.214 mole) of N,N'-bis(2,2,6,6-tetramethyl-4-piperidyl)-hexamethylenediamine and 20.0 grams (0.5 mole) of sodium hydroxide powder were charged to obtain a mixture, and the temperature of the mixture was raised to 160° C. Then, a solution containing 55.4 grams (0.20 mole) of 2,4-dichloro-6 (1,1,3,3-tetramethylbutylamino)-1,3,5-triazine in 92 grams of mixed xylenes having a boiling point of 138–141° C. was dropwise added to the mixture over a period of 4 hours.

After the dropwise addition was started, reflux of water generated in the reaction was observed. The refluxing water was distilled off. After a while, xylene refluxing started. The dropwise addition was continued for a while, and the reaction temperature started decreasing. In order to maintain the reaction temperature at 160° C. or higher, a portion of the refluxing xylene was distilled off. At the end of the dropwise addition of the solution, the total amount of the xylene distilled off was 62 grams, which means that, at the end of the addition, the xylene content in the mixture was 0.36 weight part per 1 weight part of the diamine. After the dropwise addition of the solution was completed, the reaction temperature was maintained at 160° C. for 5 hours while the water generated in the reaction was distilled off. The reaction was completed to obtain a reaction mass. Water was then added to the reaction mass to dissolve the sodium chloride generated in the reaction, and the water and sodium chloride were separated from the organic (xylene) phase. The resulting xylene solution was filtered to remove by-products and was concentrated. The resulting product was cooled to obtain a solid resin, which was then crushed.

Yield 94%

(Hereinafter, the yields are based on the amouunt of the diamine of formula (II).)

Number average molecular weight 6500 n=10.2

EXAMPLE 9

The same procedures in Example 8 were repeated except that the reaction temperature was changed to 170° C.

At the end of dropwise addition of the solution, the total amount of the xylene distilled off was 67 grams, which means that, at the end of the addition, the xylene content in the mixture was 0.29 weight part per 1 weight part of the diamine.

Yield 94%

Number average molecular weight 5700 n=8.9

EXAMPLE 10

The same procedures in Example 8 were repeated except that the amount of N,N'1-bis(2,2,6,6-tetramethyl-4-piperidyl)hexamethylenediamine was changed to 86.8 grams (0.22 mole)

Yield 93%

Number average molecular weight 4500 n=6.9

EXAMPLE 11

The same procedures in Example 8 were repeated except that amount of N,N'-bis(2,2,6,6-tetramethyl-4-piperidyl) hexamethylenediamine was changed to 82.9 grams (0.21 mole)

Yield 95%

Number average molecular weight 6900 n=10.9

EXAMPLE 12

The same procedures in Example 8 were repeated except that the 84.5 grams of N,N'-bis(2,2,6,6-tetramethyl-4-piperidyl)hexamethylenediamine was replaced by 84.5 grams of a mixture of N-(2,2,6,6-tetramethyl-4-piperidyl) hexamethylenediamine and N,N'-bis(2,2,6,6-tetramethyl-4-piperidyl)hexamethylenediamine (according to an areametric analysis measured by gas chromatography, the mixture contained 12% of N-(2,2,6,6-tetramethyl-4-piperidyl) hexamethylenediamine.).

Yield 90%

Number average molecular weight 4400 n=6.7

EXAMPLE 13

The same procedures in Example 8 were repeated except that the solution containing 55.4 grams (0.20 mole) of 2,4-dichloro-6-(1,1,3,3-tetramethylbutylamino)-1,3,5-triazine in 92 grams of the mixed xylenes was replaced by a solution containing 47.0 g (0.20 mole) of 2,4-dichloro-6-morpholino-1,3,5-triazine in 92 grams of the mixed xylenes.

Yield 91%

Number average molecular weight 2500 n=3.7

Comparative Example 1

The same procedures in Example 9 were repeated except that xylene was replaced by 110 grams of o-dichlorobenzene and that the o-dichlorobenzene was not distilled off. (But, distilling off the water was conducted.)

Yield 88%

Number average molecular weight 5400 n=8.3

Comparative Example 2

Into a 1 L four necked flask, 84.5 grams (0.214 mole) of N,N'-bis(2,2,6,6-tetramethyl-4-piperidyl)hexamethylenediamine, 20.0 grams (0.5 mole) of sodium hydroxide powder and a solution containing 55.4 grams (0.20 mole) of 2,4-dichloro-6-(1,1,3,3-tetramethylbutylamino)-1,3,5-triazine in 300 grams of toluene were charged to obtain a mixture. Then, the temperature of the mixture was raised to initiate reflux and the refluxing was continued for 16 hours. After completion of the polycondensation reaction, the by-products and salts generated in the reaction were removed by filtration. The filtrate was washed with water, concentrated and cooled whereby a solid resin was obtained. The solid resin was then crushed.

Yield 72%

Number average molecular weight 2800 n=4.0

Comparative Example 3

Into a 500 ml autoclave made of SUS 316 L, 86.8 grams (0.22 mole) of N,N'-bis(2,2,6,6-tetramethyl-4-piperidyl)hexamethylenediamine and 37 grams of 48% aqueous sodium hydroxide solution were charged to form a mixture, and the temperature of the mixture was raised to 180° C. Then, into the mixture, a solution containing 55.4 grams (0.20 mole) of 2,4-dichloro-6-(1,1,3,3-tetramethylbutylamino)-1,3,5 triazine in 98 grams of xylene was dropwise added over 4 hours. After the addition of the solution was complete, the reaction temperature was maintained at 185° C. for 5 hours. Then, after separating the aqueous and organic phases, the organic phase was washed with water and filtered to remove by-products to obtain a product. The product was concentrated and cooled to obtain a solid resin. The solid resin was then crushed. The autoclave was so eroded that it had to be disgarded.

Yield 89% number average molecular weight 4800 n=7.3

What is claimed is:

1. A process for preparing a polyaminotriazine represented by the formula (I):

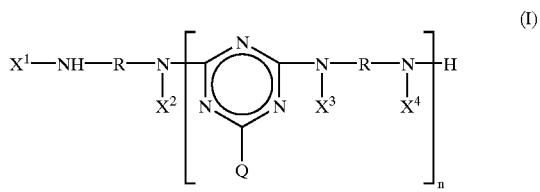

wherein n is a number from 2 to 20;

$X^1$, $X^2$, $X^3$ and $X^4$, which are the same or different, are each hydrogen or piperidyl represented by formula (Ia):

wherein $R^1$ is a hydrogen atom, $C_1$ to $C_{12}$ alkyl, $C_1$ to $C_{18}$ alkoxy, $C_3$ to $C_8$ alkenyl, $C_7$ to $C_{11}$ arylalkyl or $C_3$ to $C_5$ alkenyloxy, wherein at least 75 mole % of $X^1$, $X^2$, $X^3$ and $X^4$ is piperidyl represented by formula (Ia);

R is $C_2$ to $C_{12}$ alkylene, which can be interrupted by —O— or —$NR^2$—, wherein $R^2$ is hydrogen, $C_1$ to $C_{12}$ alkyl, $C_3$ to $C_{12}$ cycloalkyl or piperidyl represented by formula (Ia), or R is a divalent $C_6$ to $C_{15}$ cycloaliphatic group; and Q is —$OR^3$, —$NHR^4$ or —$NR^4R^5$, wherein $R^3$ is $C_1$ to $C_{12}$ alkyl, $C_5$ to $C_{12}$ cycloalkyl, benzyl, phenyl, tolyl or piperidyl represented by formula (Ia), $R^4$ is $C_1$ to $C_{12}$ alkyl, $C_3$ to $C_{12}$ alkoxyalkyl, $C_4$ to $C_{12}$ $N_1$N-dialkylaminoalkyl, $C_3$ to $C_5$ alkenyl, phenyl, benzyl, cyclohexyl, tolyl or piperidyl of the formula (Ia), and $R^5$ is $C_1$ to $C_{12}$ alkyl or cycloalkyl, or $R^4$ and $R^5$ together with the N atom to which they are bonded form a 5- or 6-membered heterocyclic ring, which comprises (a) conducting a reduction alkylamination of a tetramethylpiperidone represented by formula (IIa):

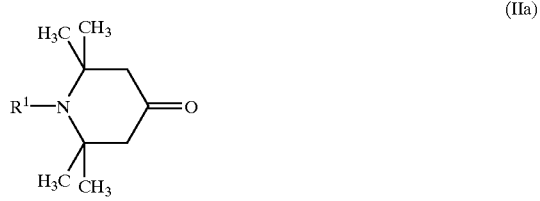

with a diamine represented by formula (IIb):

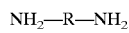

wherein R is as defined above, in the presence of hydrogen and a small but effective amount of a hydrogenation catalyst to obtain a crude product containing the catalyst;

(b) after the completion of the reduction alkylamination, separating the catalyst from the crude product to obtain a crude product (A); and (c) without refining said crude product (A), conducting a polycondensation reaction of the crude product (A) and a dichlorotriazine represented by formula (III)

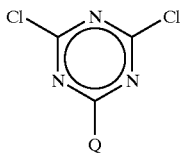

(III)

in an aromatic solvent in the presence of an inorganic base, wherein the amount of the tetramethylpiperidone of formula (IIa) is from at least 1.7 moles to less than 1.95 moles per 1 mole of the diamine of the formula (IIb).

2. A process according to claim 1, wherein the amount of the dichlorotriazine of the formula (III) is from 0.75 to about 1 mole per 1 mole of the diamine of the formula (IIb).

3. A process according to claim 1, wherein the amount of the dichlorotriazine of the formula (III) is from 0.8 to 0.9 mole per 1 mole of the diamine of the formula (IIb).

4. A process according to claim 1, wherein the crude product (A) is obtained by (i) conducting a reaction between a tetramethylpiperidone of the formula (IIa) and a dimaine of the formula (IIb) at about 50° C. to about 100° C. in the absence of a solvent while distilling off water, (ii) conducting a reduction alkylamination of the resulting product with hydrogen in the presence of a catalyst selected from the group consisting of platinum, palladium and Raney nickel to obtain a crude product containing catalyst, and (iii) thereafter, separating out said catalyst to obtain said crude product (A).

5. A process according to claim 1, wherein the crude product (A) is obtained by (i) conducting a reduction alkylamination of a tetramethylpiperidone of the formula (IIa) with a diamine of the formula (IIb) in the presence of a catalyst selected from the group consisting of platinum, palladium and Raney nickel, and in the presence of a solvent selected from the group consisting of methanol, ethanol, propanol and a mixture of any thereof with water, and, (ii) filtering off the catalyst and distilling off the solvent from (i).

6. A process according to claim 1, wherein the reduction alkylamination is conducted in the presence of 0.001 to 0.04 weight % of platinum or palladium at a temperature of from 40° C. to 140° C.

7. A process according to claim 1, wherein the reduction alkylamination is conducted in the presence of 0.1 to 30 weight % of Raney nickel, based on the tetramethylpiperidone of the formula (IIa), at a temperature of from 100° C. to 180° C.

8. A process according to claim 1, wherein the polycondensation reaction is conducted at an elevated pressure, by adding a solution of the dichlorotriazine represented by formula (III) in an aromatic solvent to a mixture of the crude product (A) and, as the inorganic base, a 50% aqueous solution of sodium hydroxide or potassium hydroxide while maintaining a temperature in the range of 145° C. to 200° C.

9. A process according to claim 1, wherein the polycondensation reaction is conducted at atmospheric pressure by adding a solution of the dichlorotriazine represented by formula (III) in an aromatic solvent to a mixture of the crude product (A) and, as the inorganic base, solid sodium hydroxide or potassium hydroxide which is kept at 145° C. to 190° C. while distilling off water and a part of the aromatic solvent.

10. A process according to claim 9, wherein the amount of the solvent present in the polycondensation is 0.1 to 1 weight part per 1 weight part of the crude product (A).

11. A process according to claim 9, wherein the mixture of the crude product (A) and solid sodium hydroxide or potassium hydroxide is kept at 155° C. to 180° C.

12. A process according to claim 9 or 11, wherein the amount of the solvent in the polycondensation is 0.2–0.8 weight part per 1 weight part of the crude product (A).

13. A process according to claim 1, wherein $R^1$ is hydrogen or methyl, R is straight chain alkylene having 2–12 carbon atoms and Q is —$NHR^4$ or —$NR^4R^5$.

14. A process according to claim 13, wherein Q is —$NHR^4$.

15. A process according to claim 14, wherein $R^1$ is hydrogen, R is hexamethylene and Q is 1,1,3,3-tetramethylbutylamino.

16. A process according to claim 1, wherein said inorganic base is sodium hydroxide or potassium hydroxide.

17. A process according to claim 1, or wherein said inorganic base is sodium hydroxide or potassium hydroxide, and said inorganic base is present in an amount of 2 to 3 moles per 1 mole of the dichlorotriazine of the formula (III).

* * * * *